US011255555B1

United States Patent
Shalvi

(10) Patent No.: US 11,255,555 B1
(45) Date of Patent: Feb. 22, 2022

(54) ULTRAVIOLET DISINFECTION DEVICE AND USES THEREOF

(71) Applicant: OLYMPIA LIGHTING, INC., Northvale, NJ (US)

(72) Inventor: Ram Shalvi, Closter, NJ (US)

(73) Assignee: OLYMPIA LIGHTING, INC., Nortivale, NJ (US)

( * ) Notice: Subject to any disclaimer, the term of this patent is extended or adjusted under 35 U.S.C. 154(b) by 0 days.

(21) Appl. No.: 17/394,586

(22) Filed: Aug. 5, 2021

Related U.S. Application Data

(60) Provisional application No. 63/186,428, filed on May 10, 2021.

(51) Int. Cl.
   *F24F 8/22* (2021.01)
   *F24F 11/88* (2018.01)
   *F24F 110/30* (2018.01)

(52) U.S. Cl.
   CPC ............ *F24F 8/22* (2021.01); *F24F 11/88* (2018.01); *F24F 2110/30* (2018.01)

(58) Field of Classification Search
   CPC ........... F24F 8/22; F24F 11/88; F24F 2110/30
   See application file for complete search history.

(56) References Cited

U.S. PATENT DOCUMENTS

| | | | |
|---|---|---|---|
| 3,744,216 A | 7/1973 | Halloran | |
| 3,750,370 A | 8/1973 | Brauss et al. | |
| 5,505,904 A | 4/1996 | Haidinger et al. | |
| 5,656,242 A * | 8/1997 | Morrow | A61L 9/12 422/120 |
| 6,464,760 B1 | 10/2002 | Sham et al. | |
| 6,494,940 B1 | 12/2002 | Hak | |
| 6,497,840 B1 * | 12/2002 | Palestro | A61L 9/20 250/432 R |
| 7,270,696 B2 | 9/2007 | Yuen | |
| 8,252,100 B2 | 8/2012 | Worrilow | |
| 8,350,228 B2 | 1/2013 | Welker | |
| 8,377,183 B2 | 2/2013 | Bailey et al. | |
| 8,562,913 B2 | 10/2013 | Searle | |

(Continued)

FOREIGN PATENT DOCUMENTS

| | | |
|---|---|---|
| CN | 103353146 A | 10/2013 |
| CN | 209262813 U | 8/2019 |

(Continued)

*Primary Examiner* — Emmanuel E Duke
(74) *Attorney, Agent, or Firm* — Law Offices of Albert Wai-Kit Chan, PLLC; Robert D. Katz, Esq.

(57) ABSTRACT

A device for generating ultraviolet (UV) radiation whose wavelength is optimally tuned into the range of 250 to 285 nm, with peak wavelength in the range of 260 to 270 nm, which attains a Peak Germicidal Disinfection Effectiveness Index of nearly 100%, superior to conventional UV lights and lamps. The device comprises an ultraviolet light-emitting diode (LED) array, an operation control system, an airflow sensor with programmable sensitivity, and a surge protection module. The device is installed in conventional HVAC systems such as air conditioning systems and HVAC ducts to effectively disinfect airflow passing through to deactivate bacteria, viruses, and mold. Depending on the operating status of the HVAC systems, the device senses airflow passing through or going around and intelligently turns on and off the ultraviolet LED array to attain a longer lifetime.

20 Claims, 6 Drawing Sheets

(56) References Cited

U.S. PATENT DOCUMENTS

| | | | |
|---|---|---|---|
| 8,926,132 B2 | 1/2015 | Horng et al. | |
| 9,308,289 B2 | 4/2016 | Graff et al. | |
| 9,517,280 B2 | 12/2016 | Lynn et al. | |
| 9,603,956 B2 | 3/2017 | Newham | |
| 9,707,310 B2 | 7/2017 | Watanabe et al. | |
| 10,039,852 B2 * | 8/2018 | Yi | F24F 1/0071 |
| 2004/0146437 A1 * | 7/2004 | Arts | F24F 3/16 |
| | | | 422/186.07 |
| 2008/0008620 A1 | 1/2008 | Alexiadis | |
| 2014/0157989 A1 * | 6/2014 | Kirschman | A61L 2/26 |
| | | | 96/224 |
| 2015/0247615 A1 * | 9/2015 | Matsui | F21V 3/04 |
| | | | 250/492.1 |
| 2017/0125683 A1 * | 5/2017 | Lee | H01L 51/0048 |
| 2017/0217791 A1 * | 8/2017 | McNulty | C02F 1/325 |
| 2017/0321877 A1 | 11/2017 | Polidoro | |
| 2018/0064840 A1 | 3/2018 | Saiki et al. | |
| 2018/0250430 A1 | 9/2018 | Machovina et al. | |
| 2018/0299117 A1 | 10/2018 | Min | |
| 2019/0009912 A1 * | 1/2019 | Matsui | B64D 13/08 |
| 2019/0076897 A1 | 3/2019 | Shingu et al. | |
| 2019/0234563 A1 | 8/2019 | Cartiere et al. | |
| 2020/0009286 A1 | 1/2020 | Zarcone et al. | |
| 2020/0030478 A1 | 1/2020 | Uchimura | |
| 2020/0309703 A1 * | 10/2020 | Luk | A61L 2/24 |

FOREIGN PATENT DOCUMENTS

| | | |
|---|---|---|
| CN | 209944154 U | 1/2020 |
| CN | 111330033 A | 6/2020 |
| CN | 111365651 A | 7/2020 |
| CN | 111536468 A | 8/2020 |
| CN | 111542149 A | 8/2020 |
| CN | 211450402 U | 9/2020 |
| EP | 2881126 A1 | 6/2015 |
| KR | 20030048989 A | 6/2003 |
| KR | 100698800 B1 | 3/2007 |
| KR | 20090078908 A | 7/2009 |
| KR | 20100119627 A | 11/2010 |
| KR | 101338130 B1 | 12/2013 |
| TW | M513332 U | 12/2015 |
| WO | 2020052506 A1 | 3/2020 |

\* cited by examiner

ULTRAVIOLET DISINFECTION DEVICE AND USES THEREOF

FIELD OF THE INVENTION

The present invention relates to lighting devices that include germicidal disinfection by ultraviolet radiation and methods of utilizing such devices for germicidal disinfection.

BACKGROUND OF THE INVENTION

Ultraviolet radiation can be used for germicidal disinfection and decontamination of air and surfaces. UV radiation is the electromagnetic radiation that falls in the region of spectrum between visible light and x-rays. UV radiation is invisible to the human eye and includes wavelengths in the spectral range of 100 to 400 nanometers (nm). This spectral range can be subdivided into four regions: vacuum UV rays with wavelengths in the range of 100 to 200 nm, UVC rays with wavelengths that range from 200 to 280 nm, UVB rays with wavelengths that range from 280 to 315 nm, and UVA rays with wavelengths that range from 315 nm to 400 nm. Because of the spectral sensitivity of DNA and RNA in bacteria and viruses, only the UVC region demonstrates significant germicidal properties. According to the 2006 U.S. EPA UV Disinfection Guidance Manual (1), recommended UVC exposure dosage, which is measured as the product of UVC light intensity multiplied by exposure time, should be at least 2,500 µLW·s/cm$^2$ and up to 8,000 µLW·s/cm$^2$ for effectively killing 90% of most bacteria and viruses.

Conventional devices using UV radiation for disinfection, such as low-pressure UV lights and/or UV lamps, may present problems with safety and effectiveness. Extensive and prolonged exposure to UV radiation may be associated with occurrence of skin cancers and may also cause problems to the health of eyes. The effectiveness index of a conventional UV lamp is typically around 80%, which does not use the UVC region most effectively. The present invention solves foregoing issues with innovative designs and optimal spectral tuning.

Traditional heating, ventilation, and air conditioning (HVAC) systems often lack function of germicidal disinfection, which has become increasingly important and perhaps a necessity given the current COVID-19 pandemic situation. The present invention is installed inside an air-handling unit such as a traditional HVAC system to supplement the HVAC system with such function. Since the UV light is not exposed to the outside of the HVAC system, it is safe to use and attains an almost 100% effectiveness index.

SUMMARY OF THE INVENTION

The present invention provides a disinfection device for an HVAC system. The device comprises an ultraviolet light array that comprises a plurality of ultraviolet light sources arranged in a predetermined pattern. The ultraviolet light array has a first end and a second end, and the device comprises a housing mounted on the first end of the ultraviolet light array. The device comprises an operation control system contained within the housing, wherein the operation control system includes means for airflow detection, means for surge protection, and a circuit configured to convert electrical power into power for the ultraviolet light array, the means for airflow detection, and the means for surge protection. The means for surge protection protects the device from voltage surges. The means for airflow detection detects airflow passing through or going around the device, such that when the rate of the airflow as detected by the means for airflow detection is above a preset and tunable threshold, the operation control system powers on the plurality of ultraviolet light sources in the ultraviolet light array. When powered on, the ultraviolet light sources emit ultraviolet radiation within the HVAC system that projects outwards and disinfects the airflow passing through or going around the device.

In one embodiment, the UV radiation generated by the light sources (e.g., LEDs, including ultraviolet LEDs) is in the wavelength range of 200 nm to 400 nm. In one embodiment, the UV radiation generated by the light sources is in the wavelength range of 260 nm to 270 nm. In another embodiment, the UV radiation generated by the light sources has peak wavelength range of 250 nm to 285 nm. In one embodiment, the UV radiation kills germs including bacteria and viruses and disinfects air passing through the HVAC system before release to the ambient environment.

BRIEF DESCRIPTION OF THE FIGURES

Further features and advantages of the embodiments of the present invention can be understood by reference to the accompanying specification taken in connection with the accompanying drawings in which.

DETAILED DESCRIPTION OF THE INVENTION

Figure 1:
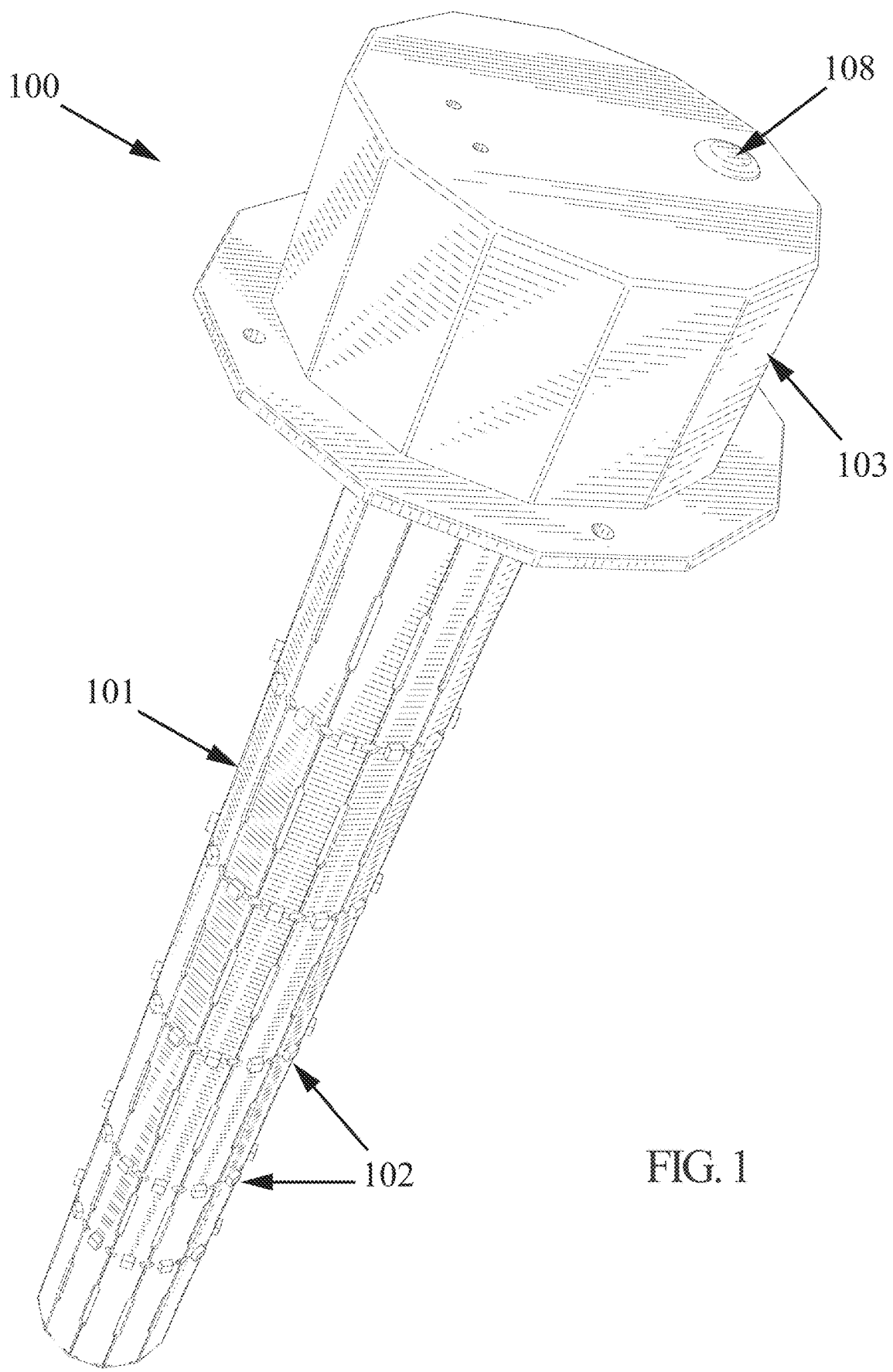
FIG. 1 is a front perspective view of one embodiment of the disinfection device of the present invention.
Figure 2:
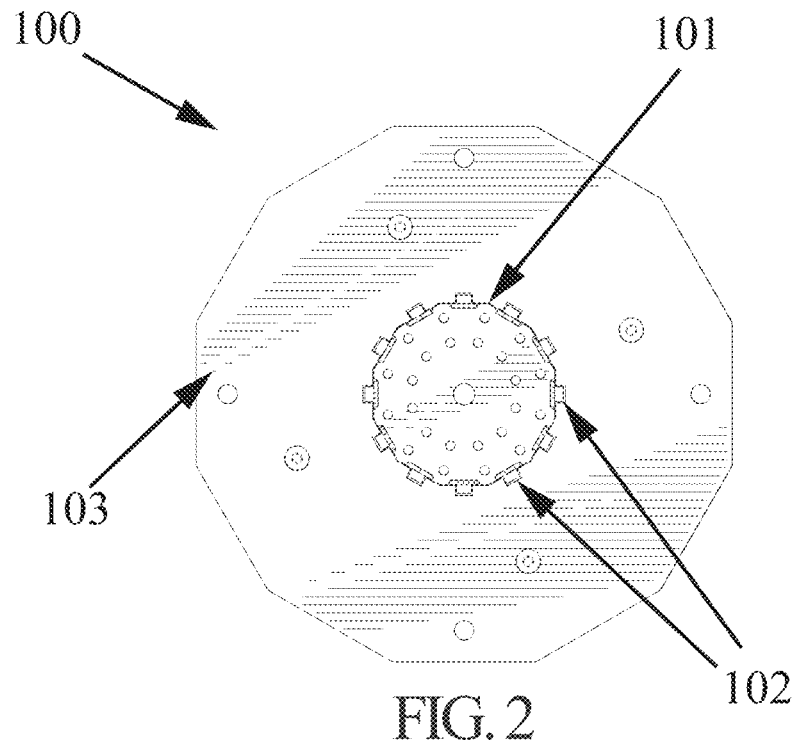
FIG. 2 is a bottom view of the disinfection device of the present invention.
Figure 3:
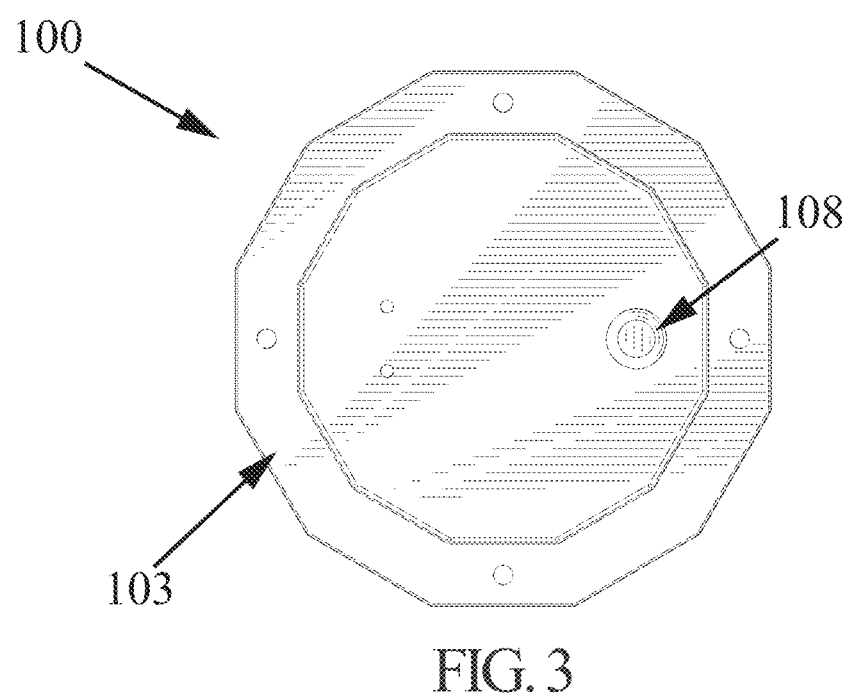
FIG. 3 is a top view of the disinfection device of the present invention.
Figure 4:
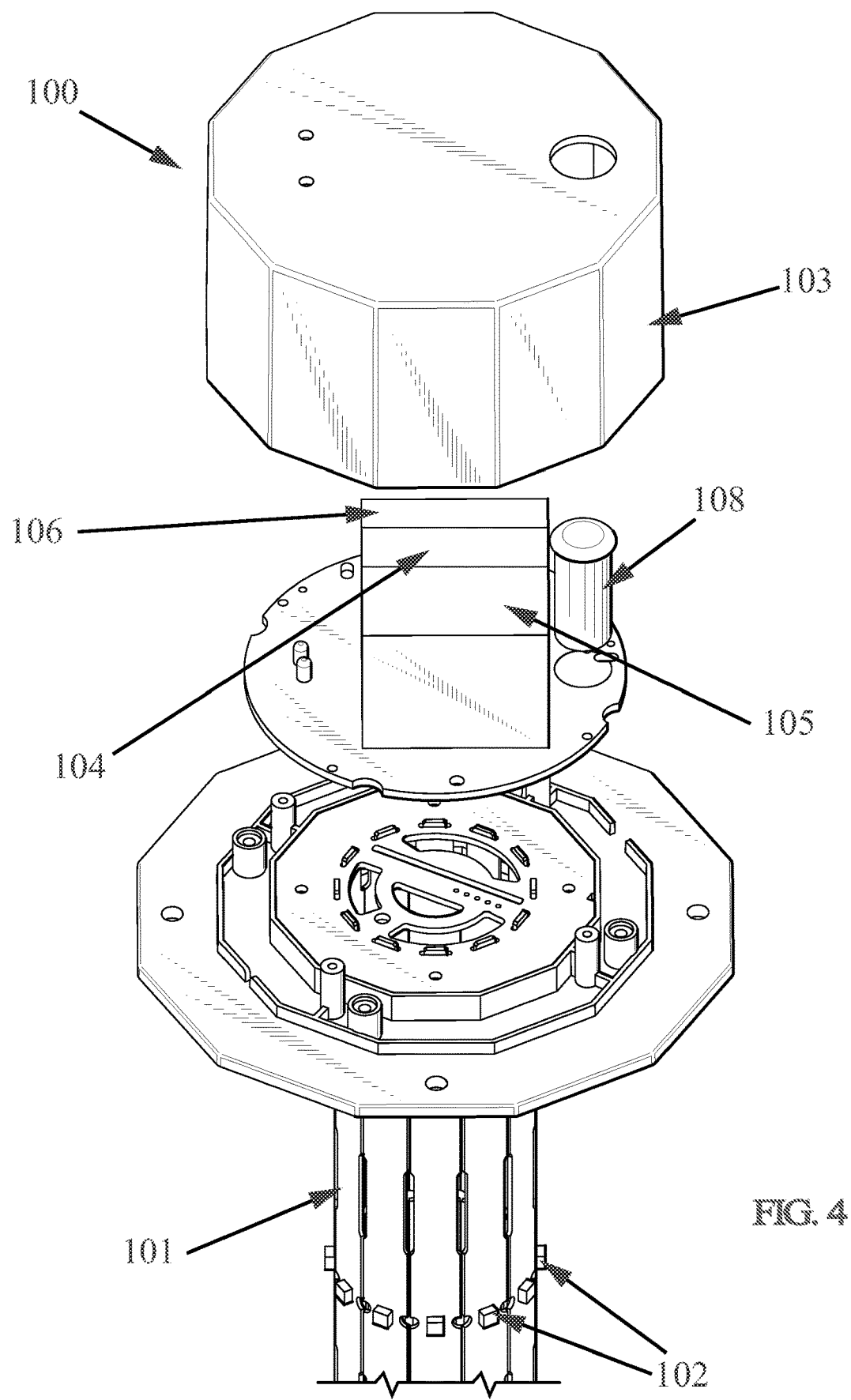
FIG. 4 is an exploded view of the disinfection device of the present invention showing the components inside the housing.
Figure 5:
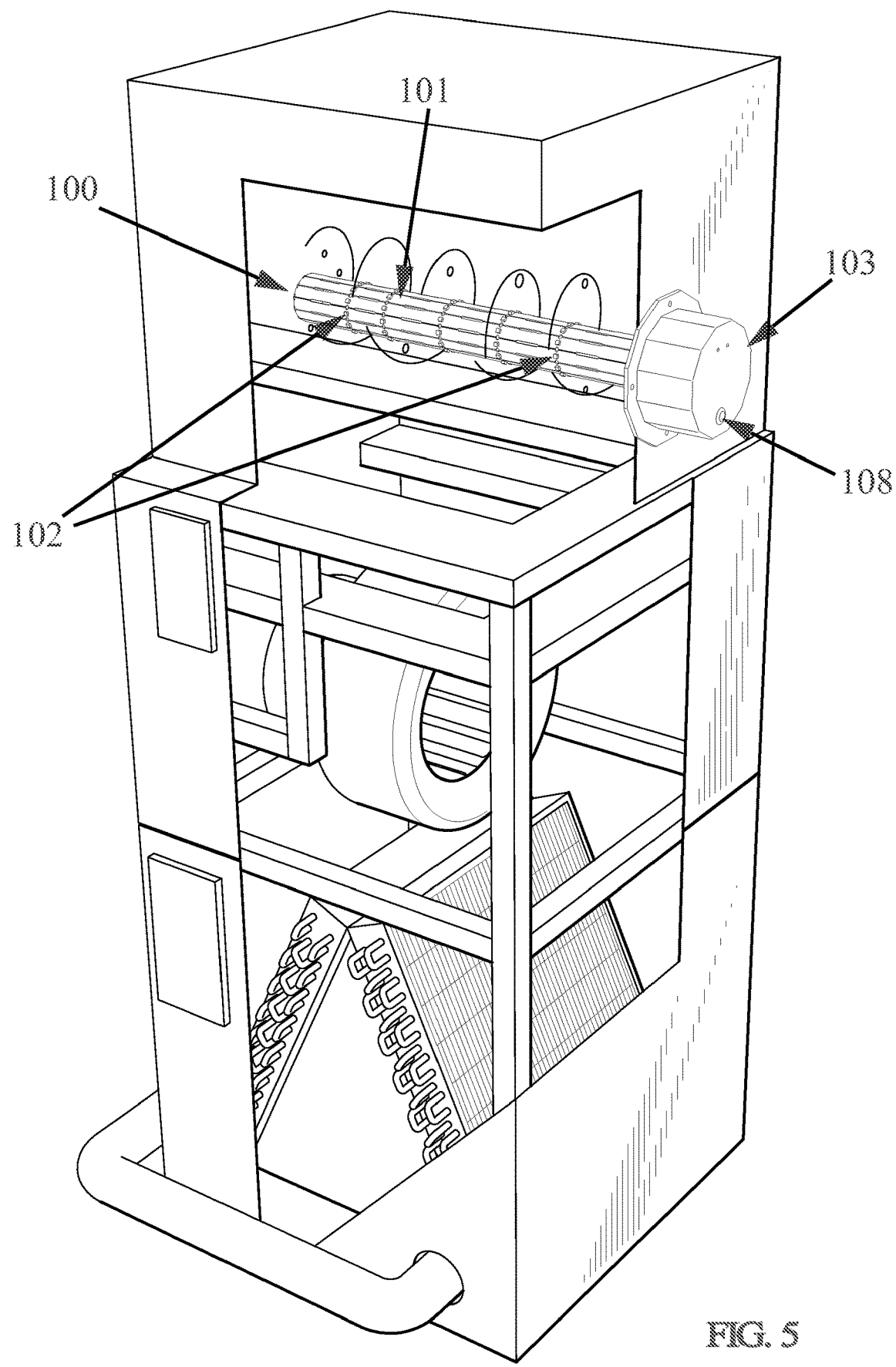
FIG. 5 is a perspective view of the disinfection device, showing how the device of the present invention is installed and operated within an HVAC system.

Referring to the drawings, FIG. 1 illustrates a preferred embodiment of the disinfection device of the present invention generally referred by the numeral 100. The device (100) comprises an ultraviolet light array (101) that in turn comprises a plurality of ultraviolet light sources (102) arranged in a predetermined pattern. The ultraviolet light array has a first end and a second end, and the device comprises a housing (103) mounted on the first end of the ultraviolet light array (101). The device comprises an operation control system (104) contained within the housing (see FIG. 5), wherein the operation control system comprising means for airflow detection (105), means for surge protection (106), and circuit (107) configured to convert electrical power into power for the ultraviolet light array (101), the means for airflow detection (105), and the means for surge protection (106). The means for surge protection (106) protects the device from voltage surge. The means for airflow detection (105) detects airflow passing through or going around the device (100), such that when the rate of the airflow as detected by the means for airflow detection (105) is above a preset and tunable threshold, the operation control system (104) powers on the plurality of ultraviolet light sources (102) in the ultraviolet light array (101). When powered on, the ultraviolet light sources (102) emit ultraviolet radiation within the HVAC system that projects outwards and disinfects the airflow passing through or going around the device (100).

The following terms shall be used to describe the present invention. In the absence of a specific definition set forth herein, the terms used to describe the present invention shall be given their common meaning as understood by those of ordinary skill in the art.

The ultraviolet light array (101) comprises a plurality of ultraviolet light sources (102), such as ultraviolet light emitting diodes (UV LEDs) (102), chosen to emit the desired optical wavelengths from visible to ultraviolet spectrum. When using UV LEDs as the ultraviolet light sources (102), the light array (101) is also termed an LED matrix (101). The light array (101) has two ends and may have any shape, such as a cube, a cuboid, a cylinder, a sphere, a disk, or other shape. The ultraviolet light sources (102) are located on the external surface of the ultraviolet light array (101) and may cover a part or all of the surface. The ultraviolet light sources (102) are arranged in a predetermined pattern, usually with fixed spacing for uniform illumination. The ultraviolet light array (101) comprises UV-LED batches that are electrically connected in parallel. In one embodiment, 6 UVC LEDs (102) are electrically connected in series to form a UV-LED batch, and various UV-LED batches are electrically connected in parallel to form the ultraviolet light array (101). In one embodiment, each batch of UVC LEDs consists of 4 to 10 UVC LEDs (102) that are electrically connected in series.

The ultraviolet light sources (102) are chosen to emit desired optical wavelengths in the ultraviolet spectrum and may be chosen to emit ultraviolet rays and visible light simultaneously, and the visible light may mimic daylight, incandescent or fluorescent bulb, and/or provide a particular color tone desired for a practical application. When powered on, the ultraviolet light sources (102) emit ultraviolet radiation with tunable wavelengths that projects outwards, illuminating and disinfecting the airflow passing through or going around the device (100) and surface area. In one embodiment, the ultraviolet light sources (102) are ultraviolet light-emitting diodes including LEDs for emitting UVC rays (for example, UVC LEDs with a spectrum of wavelengths centered at approximately 265 nm) and near UVA rays (near UVA LEDs with a wavelength of approximately 405 nm). In one embodiment, the ultraviolet light sources (102) are UV LEDs, and each UV LED comprises two or more LED chips combined into a single LED component, such that each UV LED simultaneously emits both UVC rays with a center wavelength of approximately 265 nm and near UVA rays with a wavelength of approximately 405 nm. In one embodiment, the UV light sources (102) comprise UVC LEDs and near UVA LEDs that are assembled, e.g., soldered, onto one or more PCBs in any desired combination that depends on actual needs in practice and use, wherein the UVC LEDs emit UVC rays with a center wavelength of approximately 265 nm, and the near UVA LEDs emit near UVA rays with a wavelength of approximately 405 nm, allowing flexibility in the selection and/or manipulation of a desired spectrum of wavelengths.

Existing technology for air disinfection by UV radiation, such as conventional UV lamps and UV lights, often resorts to ultraviolet quartz sleeves and tubes powered by external ballasts as the source of UV rays. Compared to the present invention using both UVC LEDs and near UVA LEDs (102), the existing technology has disadvantages due to larger dimension of the UV sleeves, fewer choices of the sleeve shape, more overheating, shorter life span, etc., so available designs are less flexible and limited. The present invention adopts UV LEDs (102) which are much smaller in size, generate less heat in operation, and last longer in use.

The brightness, effectiveness, and longevity of UV LEDs (102) are inversely proportional to their operating temperature. In one embodiment, the lifetime or longevity of the UV LEDs (102) can be increased by using a large number of such UV LEDs (102) operating at an electrical power lower than the nominal power output, so as to reduce the heat produced and maintain the ultraviolet light array (101) at an operating temperature that prevents overheating. In one embodiment, the lifetime or longevity of the UV LEDs (102) is increased to 200% of their rated life, by operating at an electrical power equal to 50% of their nominal power. In one embodiment, an Electrostatic Discharge Protection (ESD) diode is electrically connected to each of the UV LEDs (102) to protect the UV LEDs (102) from electrostatic discharge and prevent a malfunction or breakdown of the device (100) due to electrostatic discharge.

In one embodiment, the ultraviolet light sources (102) have peak wavelengths in the range of approximately 265 nm for optimal disinfection and decontamination. In one embodiment, the UV and/or UVC LED ultraviolet light sources (102) have peak wavelengths in the range of 260 to 270 nm and total optical power output of at least 60 to 80 mW when operating at 500 mA.

In one embodiment, while emitting UVC rays, the UV light sources (102) further comprise near UVA LEDs (102) configured to emit near UVA rays at an approximate wavelength of 405 nm. near UVA rays at a wavelength of approximately 405 nm are visible to the human eye, and their bactericidal effects, i.e., inactivation of bacteria such as *Escherichia, Salmonella, Shigella, Listeria,* and *Mycobacterium* species have been demonstrated in a previous study (2).

In one embodiment, the ultraviolet light sources (102) have peak wavelengths in the range of 260 to 270 nm and total optical power output of at least 60 to 80 mW when operating at 500 mA (see Table 1 below). In one embodiment, the ultraviolet wavelength of ultraviolet light sources (102) is tunable in the range of 250 to 285 nm to target certain virus strains that are more susceptible to the ultraviolet rays in this wavelength range.

TABLE 1

PEAK WAVELENGTH AND TOTAL OPTICAL POWER OUTPUT

| No. | Peak Wavelength (nm) | Minimal Total Optical Power output in mW at 500 mA |
|---|---|---|
| 1 | 260 to 270 | 80 |
| 2 | 260 to 270 | 70 |
| 3 | 260 to 270 | 60 |

In another embodiment, each ultraviolet light source (102) may attain a viewing angle of 130 degrees, a forward voltage between 5.0 and 9.0 V when operating at 500 mA, a junction-to-case thermal resistance of about 7.0 to 50° C./W, and a power dissipation rate of about 4.0 W or no greater than about 4.5 W when operating at 500 mA (see Table 2 below).

TABLE 2

CHARACTERISTICS OF THE LED MATRIX

| Characteristic | Unit | Minimum | Typical | Maximum |
|---|---|---|---|---|
| Viewing Angle | degree | | 130 | |
| Forward Voltage at 500 mA | V | 5.0 | 9.0 | |
| Thermal Resistance (junction to case) | ° C./W | | 7.0 | 50 |
| Power Dissipation at 500 mA | W | | 4.0 | 4.5 |

In one embodiment, the ultraviolet light array (101) can tolerate a continuous forward current of about 100 to 700 mA or of about 500 mA, a reverse voltage of no higher than about 5 V, a case temperature in the range of about −10 to 80° C. when operating at 500 mA, a storage temperature of about −40 to 100° C., and a junction temperature no higher than about 115° C. (see Table 3 below).

TABLE 3

ABSOLUTE MAXIMUM RATINGS OF THE DEVICE

| Characteristic | Unit | Minimum | Typical | Maximum |
|---|---|---|---|---|
| Forward Current (continuous) | mA | 100 | 500 | 700 |
| Reverse Voltage | V | | | −5 |
| Operating Case Temperature Range at 500 mA | ° C. | −10 | | 80 |
| Storage Temperature | ° C. | −40 | | 100 |
| Junction Temperature | ° C. | | | 115 |

Figure 7A:
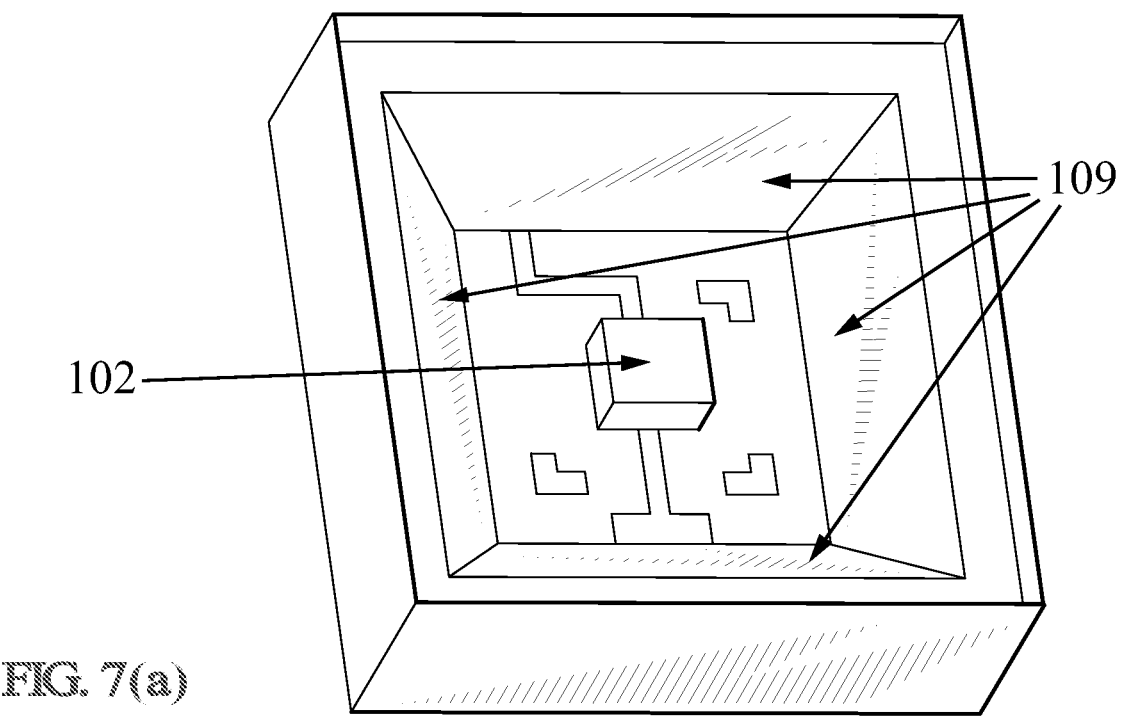
FIG. 7(a) is an enlarged view of one of the ultraviolet LEDs forming the ultraviolet light sources.
Figure 7B:
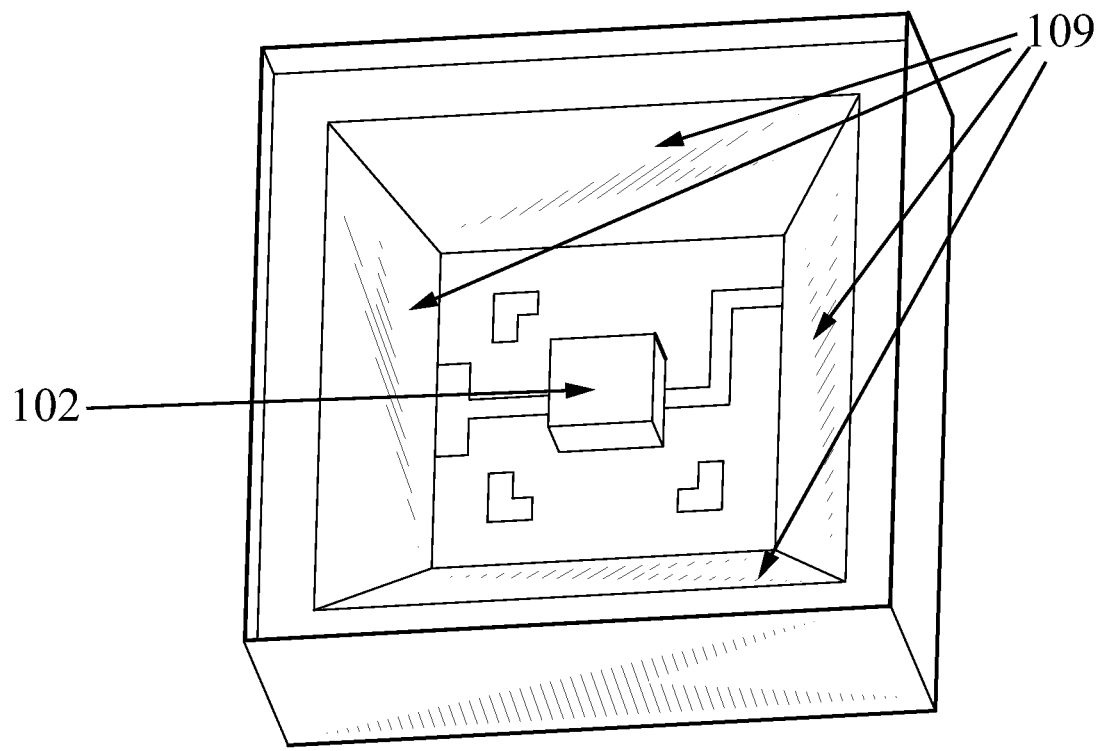
FIG. 7(b) is another enlarged view of one of the ultraviolet LEDs forming the ultraviolet light sources.

In one embodiment, as illustrated in FIGS. 7(a) and 7(b), each ultraviolet LED (102) is equipped with a number of internal mirrors (109) that are aluminum-plated or made of an artificial sapphire layer, reflecting ultraviolet rays to travel directly towards ambient air passing through or going around the device (100) of the present invention, which increases the effective ultraviolet radiation by about 12% to 20%. The aluminum plating or artificial sapphire is deposited as a thin layer onto support surfaces comprising ceramic materials, for example, in a chemical vapor deposition process. In one embodiment, the internal mirrors (109) are made of Ultraviolet (UV) Aluminum and/or Deep-UV (DUV) Aluminum which, compared to other materials such as gold and silver, yield increased reflectance for ultraviolet radiation at wavelengths of approximately 265 nm. Gold- and silver-plated mirrors (109) may increase reflectance of UV radiation at wavelengths of 120-400 nm in general; however, at wavelengths near 265 nm, their reflectance enhancement is not so efficient as the UV Aluminum or DUV Aluminum adopted in the present invention. In one embodiment, the sapphire is artificial sapphire comprising materials similar to sapphire glass crystals commonly used to cover watch faces.

In one embodiment, the ultraviolet light array (101) has a preheat or soak temperature between about 150 ($T_{smin}$) and about 200° C. ($T_{smax}$) and transitions between the limit temperatures within 60 to 120 seconds. The ultraviolet light array (101) has a liquidous temperature ($T_L$) of approximately 217° C., a maximum peak package body temperature ($T_P$) of about 260° C., a maximum ramp-up rate of 3° C./s from, and a time maintained above $T_L$ of 60 to 150 seconds ($t_L$). The ultraviolet light array (101) has a maximum ramp-down rate of 6° C./s from $T_P$ to $T_L$ and a maximum time of approximately 8 minutes from 25° C. to $T_P$ (see Table 4 below).

TABLE 4

PROFILE FEATURE AND PARAMETERS

| Parameter | Value |
|---|---|
| Preheat/Soak Minimum Temperature ($T_{smin}$) | 150° C. |
| Preheat/Soak Maximum Temperature ($T_{smax}$) | 200° C. |
| Maximum Time ($t_s$) from $T_{smin}$ to $T_{smax}$ | 60-120 seconds |
| Maximum Ramp-up Rate ($T_L$ to $T_P$) | 3° C./second |
| Liquidous Temperature ($T_L$) | 217° C. |
| Time ($t_L$) maintained above $T_L$ | 60-150 seconds |
| Maximum Peak Package Body Temperature ($T_P$) | 260° C. |
| Time ($t_P$) within 5° C. of the Specified Temperature ($T_C$) | 30 seconds |
| Maximum Ramp-down Rate ($T_P$ to $T_L$) | 6° C./second |
| Maximum Time 25° C. to Peak Temperature | 8 minutes |

In one embodiment, the ultraviolet light array (101) may have a cylindrical shape with a diameter of 3.5 to 4.5 inches and a height of $$6\frac{1}{8}$$

to 9.5 inches ultraviolet light array (101) can have a power of 30 to 150 W, a flux of 10 to 90 μW/cm², and an irradiation of 216 to 1,500 mW (see Table 5 below).

TABLE 5

PRODUCT SIZE, POWER, FLUX AND IRRADIATION

| No. | Diameter (inch) | Height (inch) | Power (W) | Flux (μW/cm²) | Irradiation (mW) |
|---|---|---|---|---|---|
| 1 | 3.5 | 6⅛ | 30 | 10 | 216 |
| 2 | 4.5 | 7 | 30 | 15 | 288 |
| 3 | 4.5 | 9.5 | 100 | 60 | 1,000 |
| 4 | 4.5 | 9.5 | 150 | 90 | 1,500 |

The housing (103) is an enclosure protecting internal components, such as the operation control system (104). In one embodiment, the housing (103) is made of metal, plastic, and/or other materials, depending on actual needs in practice and use. In one embodiment, the housing (103) is manufactured in several constituent pieces that are assembled together to form the entire housing (103). The housing (103) is mounted on one end of the ultraviolet light array (101). An ON/OFF switch (108) for manually powering the device (100) ON or OFF is accessible through an opening on the housing.

The operation control system (104), also known as an LED driver (104) when driving the LED Matrix (101), is an integrated circuit (104) enclosed within the housing (103). The operation control system (104) comprises means for airflow detection (105) and means for surge protection (106). The operation control system (104) further comprises a circuit (107) that receives electrical power and is configured to convert the electrical power into power for the ultraviolet light array (101), the means for airflow detection (105), the means for surge protection (106), and any other component of the device (100) that requires electrical power. The operation control system (104) receives sensory signals from the means for airflow detection (105), the means for surge protection (106), and any other sensors equipped within the device (100). Based on the sensory signals, the operation control system (104) computes and sends control signals to modulate the device's (100) operation and functions. In one embodiment, the operation control system (104) sends a control signal to power on the ultraviolet light array (101) when it receives a sensory signal from the means for airflow detection (105) indicating existence of airflow in the proximity of the device (100), and to power off the UV light array (101) when the means for airflow detection (105) senses a lack of airflow near the device (100). In one embodiment, the operation control system (104) sends a control signal to power off the ultraviolet light array (101), when it receives sensory signal from the means for surge protection (106) indicating a spike in electrical current, i.e., that the device (100) is at risk of a power surge. The operation control system (104) also comprises a circuit (107) for converting electrical power, such as residential power of 120 Volts, commercial power of 208 Volts, and industrial power of up-to 480 Volts, to an operating voltage of direct current (DC) suited for operating the device (100) and its components. In one embodiment, the circuit (107) is a circuit that connects to a main electrical power of alternating current (AC) ranging from 120 to 277 Volts. In one embodiment, the circuit works on universal voltage to convert worldwide applications including those from Japan (110 Volts), the United States (120 Volts), Australia and the United Kingdom (240 Volts), and industrial applications (277 Volts). In one embodiment, the circuit supplies the UVC LEDs with a DC voltage of typically about 36 Volts and usually below 50 Volts to control and ensure the UVC LEDs are working under stable and continuous operation and irradiation conditions.

In one embodiment, the operation control system (104), i.e., the LED Driver, isolates the high-voltage input (approximately 100 to 300 Volts) from the low-voltage output (lower than 50 Volts DC) to ensure safe operation in a humid environment, such that it is safe to touch by hand any electrical contacts on the UVC LEDs that might be exposed.

The means for airflow detection (105) can be an airflow sensor (105) normally equipped in an air-handling unit such as an HVAC system, a thermal management system, and a smoke/fire detection appliance. The airflow sensor may be selected from a volume airflow sensor with a spring-loaded air vane of variable resistance, a hot wire airflow sensor, and a pressure-sensor based airflow sensor. The airflow sensor (105) receives electrical power from the circuit (107). In one embodiment, when rate of airflow passing through or going around the device (100) is above a threshold, the airflow sensor (105) sends a signal indicating the existence of the airflow, indicating that the air-handling unit is in operation. The threshold is preset and tunable based on actual needs in practice and use. In one embodiment, the airflow sensor (105) sends signals indicating one of two levels (i.e., a HIGH level and a LOW level) of airflow passing through or going around the device (100), and, in accordance with the sensed airflow level, the operation control system (104) automatically adjusts the intensity of the ultraviolet rays radiated by the ultraviolet light array (101) to provide a sufficient dose of UV irradiation for effective deactivation of bacteria, viruses and mold. The airflow sensor (105) can also cause the device (100) to power off the UV light array (101) when it detects a lack of airflow.

The means for surge protection (106) detects a spike in electrical current when the ultraviolet light array, a compressor and/or a motor is turned on and sends a sensory signal to the operation control system (104). Upon receiving a power surge signal, the operation control system (104) automatically powers off the device (100) and any appliance that the device (100) is equipped with, providing protection against over-voltage damage. The means for surge protection (106) also protects the device (100) and any air-handling unit from lightning damage.

In one embodiment, the means for surge protection (106) is a temperature switch equipped with the operation control system (104). Under normal conditions, the temperature switch is closed and allows electrical current to be carried to the UVC LEDs. The temperature switch provides two functions: 1) when the temperature of the UVC LEDs is higher than a recommended working temperature of approximately 65° C., it switches to open and thus disconnects the electrical current to the UVC LEDs, allowing the latter to power off and cool down; and 2) when the HVAC system is in operation, and airflow passing through or going around the device (100) cools down the device (100) so that the temperature of the UVC LEDs is maintained below the recommended working temperature, the temperature switch remains closed to sustain the electrical current to the UVC LEDs. In one embodiment, when airflow stops passing through or going around the device (100) once the HVAC system is shut down or non-operational, due to a rise in the temperature of the UVC LEDs above the recommended working temperature, the temperature switch reactively opens the circuit and cuts off the electrical current to the UVC LEDs. This feature regulating the working temperature of the UVC LEDs extends the life of the UVC LEDs. In one embodiment, the life of the UVC LEDs is extended by a factor of two or more, thanks to the temperature-regulating feature that lowers the operating temperature of the UVC LEDs.

Compared to conventional quartz UV tubes and UV lamps with average lifetime of about 8,000 hours, the ultraviolet light sources (102) of the present invention attain a much longer lifetime by intelligently turning on and off during operation. In one embodiment, the ultraviolet light sources (102) are UV LEDs that have a rated life of up to 30,000 to 50,000 hours (measured as the time of use after which the UV LEDs optical output decreases to 70% of the original value), which is about 2.5 to 5 times superior to that of typical quartz tubes.

Conventional UV lights and/or lamps rely on UVC radiation at a wavelength of approximately 254 nm and may only achieve Peak Germicidal Disinfection Effectiveness (PGDE) Index of approximately 80%. Compared to those conventional UV lights and/or lamps, the device (100) of the present invention optimally tunes the wavelength of UVC radiation in the range of 250 to 300 nm and achieves a PGDE Index of almost 100%.

Figure 6:
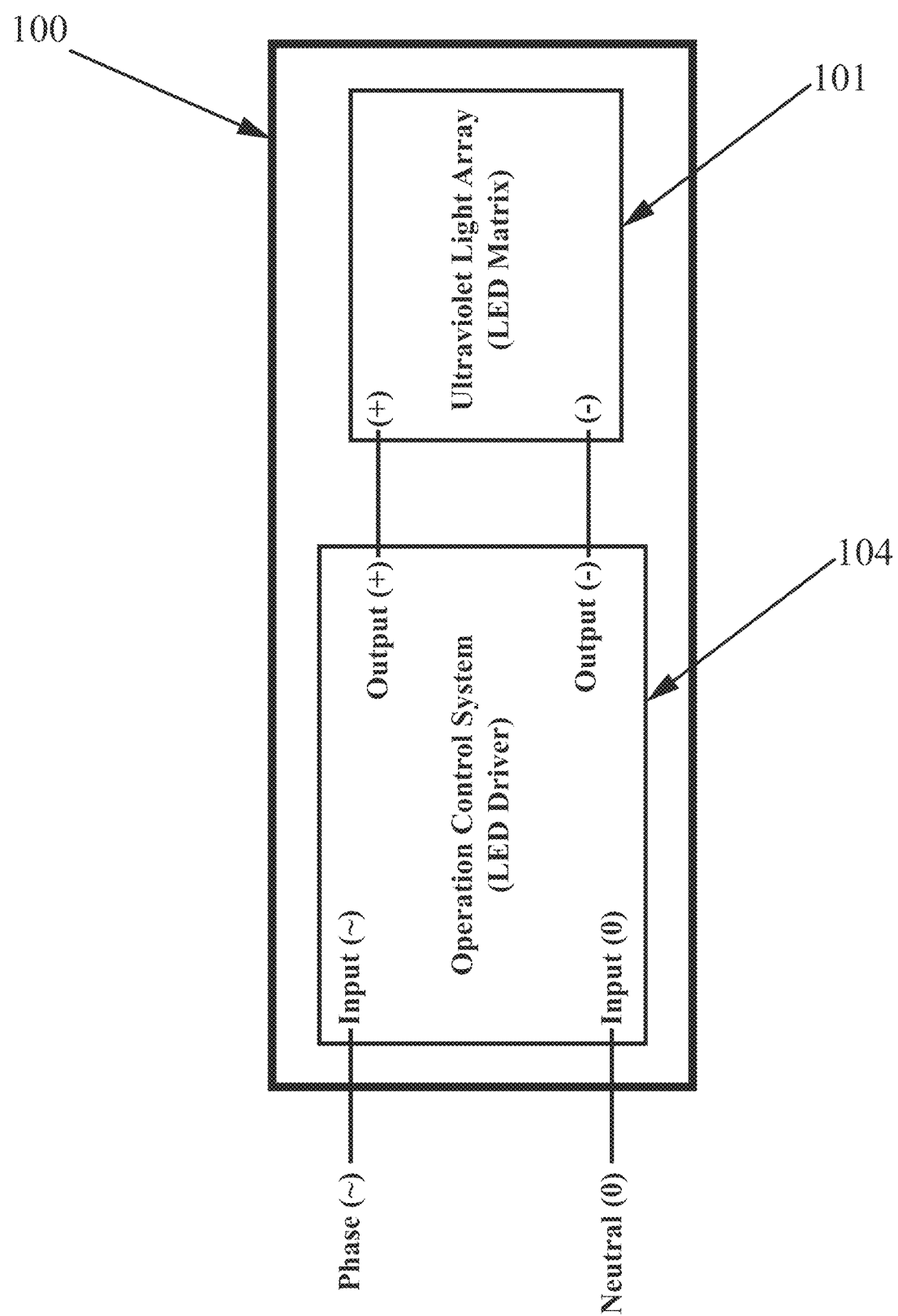
FIG. 6 is a block diagram illustrating the electrical connections among the ultraviolet light array, the operation control system, and the main electrical power source.

Compared to conventional UV lights/lamps, the disinfection device (100) of the present invention provides safety protection from UV hazard. Exposure to UV radiation can be dangerous and is associated with damage to eyesight and incidence of skin cancers, and users of UV lights/lamps should be protected from direct exposure of UV radiation. A user can avoid exposure to UV radiation when using the device (100) of the present invention, as the UV light array (101) is concealed within the HVAC system as shown in FIG. 6.

The device (100) of the present invention disinfects air passing through or going around the surfaces of the UV light array (101) and circulated through the device (100). The device (100) may be installed and operated inside an air-handling unit, such as a conventional HVAC system, and the device (100) can disinfect the airflow circulated through the HVAC system. The device (100) of the present invention is compatible with and thus provides disinfection as an add-on feature for conventional HVAC systems, whether residential, commercial, or industrial.

The device (100) of the present invention may disinfect surfaces and air within a distance of 3 to 5 meters and achieve an almost 100% PGDE Index after a continuous use for 10 to 30 minutes.

The device (100) of the present invention can be equipped in an HVAC duct for disinfecting air circulation inside the HVAC system. The device (100) of the present invention is equipped with an indicator light showing its status of operation. In one embodiment, the indicator is an LED light that is on when the device (100) is in operation.

In one embodiment, the present invention provides a solution for surface disinfection through UVC irradiation that can only occur with a line of sight between the UVC Source and the Surface.

In one embodiment, the device (100) provides surface and air disinfection for airborne viruses.

In one embodiment, the present device (100) has one or more thermal sensors (thermistors) coupled to switches integrated into the circuit (107) that senses critical components' temperature and manages electrical power to protect the device (100) and its components from overheating.

In one embodiment, the present invention illustrates a built-in Surge Protection Device (SPD) to protect the device (100) from electrical surge. In one embodiment, the SPD comprises an SPD PCB connected to a fuse, a metal oxide varistor (MOV), and a GDT or arrester.

In one embodiment, the device (100) of the present invention can be instantly turned on or off. In one embodiment, the wavelength of the UV radiation can be tuned from 250 nm to 285 nm.

In one embodiment, the device (100) has a longer lifetime, approximately 30,000 hours, superior to Quartz UV Tubes and Lamps, which is usually around 8,000 hours.

In one embodiment, the device (100) monitors the airflow inside the HVAC duct and activates strong enough UVC radiation emitted by the ultraviolet light sources (102) to deactivate microorganisms such as bacteria, viruses, and mold.

In one embodiment, the device (100) has a built-in detection of airflow and automatic activation of the ultraviolet light array (101).

In one embodiment, the ultraviolet light sources (102) are only activated when airflow is being detected, which increases the device's lifetime by 2 to 3 times or even longer.

In one embodiment, the device (100) has a built-in wide voltage range 100-480V circuit (107) for quick and simple installation. The device may be powered by plugging it into a conventional electrical outlet, or it can be configured and wired such that it receives power through the HVAC system into which it is installed.

In one embodiment, the device (100) has magnets or clamps as mounts.

In one embodiment, the means for surge protection (106) comprises a thermal sensor for detecting temperature of the device (100), wherein the thermal sensor is coupled to the circuit (107). Once the temperature reaches or is higher than a predetermined temperature, the circuit (107) provides a signal to prevent the device (100) from overheating; and, after switching on, the ultraviolet light sources (102) emit ultraviolet radiation that projects outwards within the HVAC housing or ductwork and disinfects adjacent surfaces and air.

In one embodiment, the present invention provides a disinfection device (100) for an HVAC system that comprises an elongated cylindrically shaped ultraviolet light array (101) comprising a plurality of ultraviolet light sources (102) arranged in a predetermined pattern, the ultraviolet light array (101) having a first end and a second end, wherein the ultraviolet light sources (102) are ultraviolet light emitting diodes (LEDs). The device (100) also comprises a housing (103) mounted on the first end of the ultraviolet light array (101) and an operation control system (104) contained within the housing. The operation control system (104) comprises means for airflow detection (105), means for surge protection (106), and a circuit (107) to convert electrical power into power for the ultraviolet light array (101), the means for airflow detection (105), and the means for surge protection (106). The means for surge protection (106) protects the device (100) from a voltage surge, and the means for airflow detection (105) detects airflow passing through or going around the device (100), such that when the rate of the airflow as detected by the means for airflow detection (105) is above a preset and tunable threshold, the operation control system (104) powers on the plurality of ultraviolet light sources (102) in the ultraviolet light array (101). When powered on, the ultraviolet light sources (102) emit ultraviolet radiation within the HVAC system such that the ultraviolet radiation projects outwards and disinfects the airflow passing near or around the device.

In one embodiment, each of the ultraviolet light emitting diodes (102) includes a plurality of associated mirrors (109) that are aluminum-plated or sapphire-containing materials. The mirrors (109) are positioned to reflect ultraviolet rays so that they travel outwardly towards the airflow passing near and around the device, thereby increasing ultraviolet radiation received by the airflow by 12 to 20%.

In one embodiment, the circuit (107) provides a signal to the ultraviolet light array (101) to adjust its electrical power, turn on or adjust the electrical power of the means for surge protection (106), or both, to prevent the device (100) from overheating.

In one embodiment, airflow passing around and near the device (100) within the HVAC system reduces the operating temperature of the device (100).

In one embodiment, the circuit (107) is an integrated circuit and works on universal voltage from 100 to 480 volts on AC power or 120V to 750 volts on DC power.

In one embodiment, the ultraviolet light array (101) and the housing (103) are mounted with their longitudinal axes aligned.

In one embodiment, the ultraviolet light array (101) is arranged as an LED strip.

In one embodiment, the ultraviolet radiation has a wavelength in the range of 240 to 290 nm, and a peak wavelength in the range of 260 nm to 270 nm.

In one embodiment, the means for surge protection (106) is an integrated Surge Protection Device (SPD) that protects the device from an electrical surge during operation.

In one embodiment, the ultraviolet radiation has a peak wavelength in the range of 260 nm to 270 nm, and each of the ultraviolet LED light sources (102) in the ultraviolet light array (101) has a total optical power output of at least 60 to 80 mW when operating at 500 mA, or at least 10 to 30 mW when operating at 100 mA.

In one embodiment, the ultraviolet light array (101) has an elongated cylindrical shape, and the ultraviolet light array (101) has an electric power of 30 to 150 W, a luminous flux of 10 to 90 $\mu W/cm^2$ at a distance of one meter, and a power of irradiation is 200 to 4,500 mW.

In one embodiment, the device (100) has a Peak Germicidal Disinfection Effectiveness (PGDE) Index in a range of 85%-100%.

In one embodiment, the device (100) effectively reduces COVID-19 Virus by 99.9% in airflow within the HVAC system when irradiated by the device (100).

In one embodiment, each of the ultraviolet light sources (102) attains a viewing angle of 90 to 130 degrees, a forward voltage between 5.0 and 9.0 V when operating at 100 to 500 mA, a junction-to-case thermal resistance of 7 to 50° C./W, and a power dissipation ranging from 4.0 W to 4.5 W when operating at 500 mA or about 1 W at 100 to 150 mA.

In one embodiment, the ultraviolet light array (101) tolerates a continuous forward current of 100 to 700 mA, a reverse voltage of no higher than 5 V, a case temperature in the range of about −10 to 100° C. when operating at 500 mA, a storage temperature of about −40 to 100° C., and a junction temperature no higher than about 115° C.

In one embodiment, the ultraviolet light array (101) emits UVC radiation with a wavelength in the range of about 200 to 280 nm and UVA radiation with a wavelength of approximately 405 nm.

In one embodiment, the present invention provides a method for disinfecting ambient air flowing through an HVAC system. The method comprises (a) providing a disinfection device (100) having an elongated cylindrically shaped array (101) of UVC LEDs (102), a housing (103) at one end of the device (100), wherein the housing (103) contains an operation control system (104), a circuit (107) for power conversion, means for airflow detection (105), and means for power surge protection (106);

(b) installing the disinfection device (100) in the HVAC system or ductwork thereof; and (c) powering the disinfection device (100) to enable the disinfection device (100) to emit UVC and UVA radiation when the means for airflow detection (105) detects airflow above a predetermined threshold.

In one embodiment, the method achieves a Peak Germicidal Disinfection Effectiveness (PGDE) Index in a range of 85%-100%.

In one embodiment, when applying the method for disinfecting ambient air flowing through an HVAC system, the UVC radiation has a wavelength in the range of about 240 to 290 nm, and a peak wavelength in the range of about 260 nm to 270 nm.

In one embodiment, the method effectively reduces COVID-19 Virus in the airflow within the HVAC system by about 99.9%.

Throughout this application, various references or publications are cited. Disclosures of these references or publications in their entireties are hereby incorporated by reference into the application in order to more fully describe the state of the art to which this invention pertains. It is to be noted that the transitional term "comprising", which is synonymous with "including", "containing" or "characterized by", is inclusive or open-ended, and does not exclude additional, unrecited elements or method steps.

REFERENCES

1. *Ultraviolet Disinfection Guidance Manual for the Final Long Term* 2 *Enhanced Surface Water Treatment Rule*. EPA 815-R-06-007. United States Environmental Protection Agency (November 2006).
2. Murdoch et al., *Bactericidal Effects of* 405 *nm Light Exposure Demonstrated by Inactivation of Escherichia, Salmonella, Shigella, Listeria, and Mycobacterium Species in Liquid Suspensions and on Exposed Surfaces*. Scientific World J. Vol 2012, Article ID 137802 (2012).

What is claimed is:

1. A disinfection device for heating, ventilation, and air conditioning (HVAC) system, the system comprising:

an elongated cylindrically shaped ultraviolet light array comprising a plurality of ultraviolet light sources arranged in a predetermined pattern, the ultraviolet light array having a first end and a second end, wherein the ultraviolet light sources are ultraviolet light emitting diodes (LEDs);

a housing mounted on the first end of the ultraviolet light array; and an operation control system contained within the housing; wherein the operation control system comprises means for airflow detection, means for surge protection, and a circuit to convert electrical power into power for the ultraviolet light array, the means for airflow detection, and the means for surge protection; and wherein the means for surge protection protects the device from a voltage surge; the means for airflow detection detects airflow passing through or going around the device, such that when the rate of the airflow as detected by the means for airflow detection is above a preset and tunable threshold, the operation control system powers on the plurality of ultraviolet light sources in the ultraviolet light array; and, when powered on, the ultraviolet light sources emit ultraviolet radiation within the HVAC system such that the ultraviolet radiation projects outwards and disinfects the airflow passing near or around the device.

2. The device of claim 1, wherein each of the ultraviolet light emitting diodes includes a plurality of associated mirrors that are aluminum-plated or sapphire-containing materials, the mirrors positioned to reflect ultraviolet rays so that they travel outwardly towards the airflow passing near and around the device, thereby increasing ultraviolet radiation received by the airflow by 12 to 20%.

3. The device of claim 1, wherein the circuit provides a signal to the ultraviolet light array to adjust its electrical power, turn on or adjust the electrical power of the means for surge protection, or both, to prevent the device from overheating.

4. The device of claim 3, wherein airflow passing around and near the device within the HVAC system reduces the operating temperature of the device.

5. The device of claim 1, wherein the circuit is an integrated circuit and works on universal voltage from 100 to 480 volts on AC power or 120V to 750 volts on DC power.

6. The device of claim 1, wherein the ultraviolet light array and the housing are mounted with their longitudinal axes aligned.

7. The device of claim 1, wherein the ultraviolet light array is arranged as an LED strip.

8. The device of claim 1, wherein the ultraviolet radiation has a wavelength in the range of 240 to 290 nm, and a peak wavelength in the range of 260 nm to 270 nm.

9. The device of claim 1, wherein the means for surge protection is an integrated Surge Protection Device (SPD) that protects the device from an electrical surge during operation.

10. The device of claim 1, wherein the ultraviolet radiation has a peak wavelength in the range of 260 nm to 270 nm, and each of the ultraviolet LED light sources in the ultraviolet light array has a total optical power output of at least 60 to 80 mW when operating at 500 mA, or at least 10 to 30 mW when operating at 100 mA.

11. The device of claim 1, wherein the ultraviolet light array has an elongated cylindrical shape, and the ultraviolet light array has an electric power of 30 to 150 W, a luminous flux of 10 to 90 μW/cm$^2$ at a distance of one meter, and a power of irradiation is 200 to 4,500 mW.

12. The device of claim 1, wherein the device has a Peak Germicidal Disinfection Effectiveness (PGDE) Index in a range of 85%-100%.

13. The device of claim 1, wherein the device effectively reduces COVID-19 Virus by 99.9% in airflow within the HVAC system when irradiated by the device.

14. The device of claim 1, wherein each of the ultraviolet light sources attains a viewing angle of 90 to 130 degrees, a forward voltage between 5.0 and 9.0 V when operating at 100 to 500 mA, a junction-to-case thermal resistance of 7 to 50° C./W, and a power dissipation ranging from 4.0 W to 4.5 W when operating at 500 mA or about 1 W at 100 to 150 mA.

15. The device of claim 1, wherein the ultraviolet light array tolerates a continuous forward current of 100 to 700 mA, a reverse voltage of no higher than 5 V, a case temperature in the range of about −10 to 100° C. when operating at 500 mA, a storage temperature of about −40 to 100° C., and a junction temperature no higher than about 115° C.

16. The device of claim 1, wherein the ultraviolet light array emits ultraviolet-C (UVC) radiation with a wavelength in the range of about 200 to 280 nm and ultraviolet-A (UVA) radiation with a wavelength of approximately 405 nm.

17. A method for disinfecting ambient air flowing through heating, ventilation, and air conditioning (HVAC) system, comprising:

providing a disinfection device having an elongated cylindrically shaped array of ultraviolet-C light emitting diodes (UVC LEDs), a housing at one end of the device, the housing containing an operation control system, a circuit for power conversion, means for airflow detection, and means for power surge protection;

installing the disinfection device in the HVAC system or ductwork thereof; and powering the disinfection device to enable the disinfection device to emits ultraviolet-C (UVC) and ultraviolet-A (UVA) radiation when the means for airflow detection detects airflow above a predetermined threshold.

18. The method of claim 17, wherein the method achieves a Peak Germicidal Disinfection Effectiveness (PGDE) Index in a range of 85%-100%.

19. The method of claim 17, wherein the UVC radiation has a wavelength in the range of about 240 to 290 nm, and a peak wavelength in the range of about 260 nm to 270 nm.

20. The method of claim 17, wherein the method effectively reduces COVID-19 Virus in the airflow within the HVAC system by about 99.9%.

* * * * *